United States Patent [19]

Hamashima et al.

[11] Patent Number: 4,933,443
[45] Date of Patent: Jun. 12, 1990

[54] METHOD FOR PREPARING CRYSTALLINE HYDRATE OF ORAL CELPHALOSPORIN AND ITS COMPOSITION

[75] Inventors: Yoshio Hamashima, Kyoto; Kyoji Minami, Nara; Kyozo Kawata; Teruo Sakamoto, both of Osaka; Toyohiko Takeda, Hyogo; Yusuke Suzuki, Osaka; Masanori Tujikawa, Nara, all of Japan

[73] Assignee: Shionogi & Co., Ltd., Osaka, Japan

[21] Appl. No.: 275,093

[22] Filed: Nov. 21, 1988

Related U.S. Application Data

[62] Division of Ser. No. 68,333, Jul. 1, 1987.

[30] Foreign Application Priority Data

Jul. 2, 1986 [JP] Japan .................................. 61-156954
Sep. 12, 1986 [JP] Japan .................................. 61-216260

[51] Int. Cl.$^5$ .................. C07D 501/24; A61K 31/545
[52] U.S. Cl. .................................................... 540/222
[58] Field of Search .......................... 540/222; 514/202

[56] References Cited

U.S. PATENT DOCUMENTS 4,820,833  4/1989  Crisp et al. .......................... 540/222

Primary Examiner—Nicholas S. Rizzo
Attorney, Agent, or Firm—Wenderoth, Lind & Ponack

[57] ABSTRACT

An antibacterial, 7β-[(Z)-2-(2-aminothiazol-4-yl)-4-carboxybut-2-enoylamino]-3-cephem-4-carboxylic acid is stable in a (di or tri)-hydrate crystal form. A pharmacologically effective amount of this hydrate is filled in a gelatin hard capsule and sealed by a band of gelatin to make a stable composition for clinical use after storage for a long time.

8 Claims, No Drawings

METHOD FOR PREPARING CRYSTALLINE HYDRATE OF ORAL CELPHALOSPORIN AND ITS COMPOSITION

This application is a division of application Ser. No. 068,333, filed July 1, 1987 now Pat. No. 4,812,561.

This invention relates to a stable antibacterial containing 7β-[(Z)-2-(2-aminothiazol-4-yl)-4-carboxybut-2-enoylamino]-3-cephem-4-carboxylic acid (hereinafter referred to 7432-S). More specifically, it relates to a hydrate of the said compound and a stable capsule composition of the said antibacterial.

[OBJECT AND FIELD OF THIS INVENTION]

This invention provides a stable crystalline (di or tri)-hydrate of 7432-S, an oral cephalosporin useful, e.g., for treating or preventing bacterial infections.

This invention further provides a stable composition of a pharmacologically effective amount of the 7432-S hydrate in a gelatin hard capsule sealed with a band of gelatin around the circumference at the joint of cap and body of capsule.

[CLOSEST PRIOR ARTS]

The parent compound, 7432-S, useful for its broad spectrum of a high potency against Gram-positive and -negative bacteria was disclosed in Japanese Patent Application (Kokai) 60-78 987, which is equivalent to U.S. Pat. No. 4,634,697 and No. 4,748,170.

A capsule composition protected by sealing with a gelatin is written in Japanese Utility Model Publication 45-20800 which discloses a method for filling and sealing a liquid in a capsule

[PROBLEMS TO BE SOLVED BY THIS INVENTION]

It was found that the parent compound, 7432-S, was unstable even in a crystalline form to loose its potency or change its color by standing for a long time. After repeated investigations the reason was found to be that the compound was prepared by drying under reduced pressure over phosphorus pentoxide in a conventional manner to leave anhydrous material in the said prior art. Further studies applying some usual stabilizing methods (e.g., addition of a stabilizing agent, dry-granulation of water-unstable antibacterials, film coating of granules) could not stabilize the antibacterial satisfactorily. For clinical use of this compound, more stable form was required.

[SUMMARY OF THIS INVENTION]

The inventors found that
(1) crystalline 7432-S hydrate showed constant X-ray diffraction pattern and high chemical stability and
(2) the hydrate filled in a gelatin hard capsule sealed with a gelatin band around the circumference at the joint of cap and body of the capsule can be protected from the color change and potency loss. The technique was known to be useful for capsules containing liquid and not for solid powder as in this invention.

[I]

HYDRATES

[The crystalline hydrate]

The inventors seeked for a measure to improve the stability of 7432-S and found that crystalline hydrate prepared under a specific condition showed almost the same X-ray diffraction pattern and high chemical stability to enable the storage for a long time. This discovery led to this invention.

[Characteristics of the crystalline hydrate]

This crystalline hydrate is faint yellowish white to pale yellowish white microcrystalline powder.

The elemental analysis of the crystals shows the hydrate contains 2 moles of crystal water plus up to 1 mole of additional crystal water depending on the condition of, e.g., crystallizing and drying.

The content of water determined by Karl-Fischer method was in the range of 7 to 14% (especially 8.7 to 12.5%) which corresponds to (di to tri)-hydrate or a mixture of these.

The thermogram at atmospheric pressure shows that the first and second molecules of water are retained up to about 140° C., but the third molecule of water is lost at from 30° to 60° C.

Above facts are explained to show that the third molecule of water is loosely bound in the crystalline structure and lost easily (by, e.g., heat, low humidity or reduced pressure).

Every crystalline hydrate in above range of water content (i.e., in the range of dihydrate to trihydrate) shows almost the same X-ray diffraction pattern as shown on Table 1.

TABLE 1

The X-ray diffraction pattern was observed under the following condition: X-ray: wave length λ = 1.5418Å (Cupper Kα; Ni-filter) 40 kV-20 mA. The lattice spacing d is expressed in Å unit. The relative strength $I/I_o$ shows percent of strength at 20.95 Å.

| d | $I/I_o$ | d | $I/I_o$ | d | $I/I_o$ | d | $I/I_o$ |
|---|---|---|---|---|---|---|---|
| 5.90 | 12 | 20.95 | 100 | 28.70 | 17 | 35.93 | 8 |
| 7.35 | 8 | 21.15 | 70 | 29.40 | 27 | 36.38 | 24 |
| 9.45 | 92 | 21.75 | 25 | 29.60 | 11 | 37.00 | 7 |
| 10.15 | 21 | 22.25 | 49 | 29.90 | 16 | 38.30 | 26 |
| 12.08 | 46 | 23.85 | 62 | 30.40 | 19 | 38.65 | 10 |
| 14.87 | 30 | 24.50 | 39 | 31.10 | 53 | 39.20 | 15 |
| 15.65 | 14 | 24.80 | 16 | 31.60 | 23 | 39.60 | 21 |
| 16.25 | 13 | 25.50 | 34 | 31.78 | 34 | 40.27 | 15 |
| 18.35 | 24 | 25.85 | 66 | 33.02 | 28 | 41.22 | 22 |
| 18.90 | 71 | 26.60 | 16 | 33.55 | 23 | 42.55 | 8 |
| 19.14 | 77 | 27.02 | 59 | 33.86 | 17 | 44.20 | 9 |
| 19.40 | 60 | 27.30 | 35 | 35.20 | 16 | | |
| 20.58 | 88 | 28.35 | 54 | 35.65 | 10 | | |

The crystalline hydrate of this invention contains 96 to 100% (especially 99.0 to 99.8%) of cis-geometric isomer (i.e., (Z)-geometric isomer) at the 7-side chain double bond regardless to the ratio in the starting material.

The crystalline hydrate of this invention shows a strong absorption band at 1700 cm$^{-1}$ in IR-absorption spectrum observed in potassium bromide disc. This band is not found in the case of anhydrous crystals.

[Process for producing the crystalline hydrate]

(1) General Procedure

The crystalline hydrate can be prepared by the following method: the starting 7432-S is dissolved in aqueous acid and pH of the solution is raised (especially to pH 1.5 to 5.0) at about room temperature (especially 0° to 70° C.) to separate crystals. If required, the mixture is stirred to complete crystallization. The wet crystals are separated and dried at about room temperature under about atmospheric pressure in an inert gas of relative humidity of not lower than 15%.

(2) Starting Material

The starting material can be wet or anhydrous. It may be a free compound or a salt at amino (e.g., acid addition salt) or carboxy (e.g., alkali metal salt). The process of this invention in combination with the pretreatment (e.g., purification, isomerization to cis isomer, isolation) using a water soluble salt (e.g., alkali metal salt, hydrochloride) as the starting material to obtain an aqueous acid solution is a preferable embodiment of this invention.

(3) Acid

The aqueous acid solution of 7432-S can be prepared by suspending the free acid or an ammonium salt or by dissolving a carboxylate salt as the starting material in water, followed by adding acid. The said acid can be an inorganic acid (e.g., hydrochloric acid, sulfuric acid, phosphoric acid), carboxylic acid (e.g., acetic acid, malic acid, fumaric acid, citric acid), sulfonic acid (e.g., methanesulfonic acid, ethanesulfonic acid, toluenesulfonic acid), acidic salt (e.g., dimethylamine hydrochloride, 7432-S sulfate) or the like hydrophilic acid capable of acidifying the aqueous solution of the starting material. About 0 to 20 (especially 1 to 10) molar equivalents of the acid can preferably be used.

(4) Co-solvent

The aqueous solution can contain 0 to 70% of a water miscible organic solvent, for example, an alcohol (e.g., methanol, ethanol, isopropanol, t-butanol, methoxyethaol), amide (e.g., dimethylformamide), nitrile (e.g., acetonitrile), sulfoxide (e.g., diemthylsulfoxide), ether (e.g., dioxane, tetrahydrofuran, dimethoxyethane), ketone (e.g., acetone, methyl ethyl ketone), or the like as a co-solvent.

(5) Concentration

The concentration of the starting material in the aqueous acid solution can preferably be in the range 2.0 to 15.0% (especially 3.0 to 5.0%).

(6) Neutralization

A base (solid or liquid) which is capable of neutralizing the aqueous acid solution to the predetermined pH can be used for adjusting an aqueous acid solution at room temperature (about 0° to 70° C., especially 10° to 50° C.) to about isoelectric point (pH about 1.5 to 5.0, especially 2.0 to 3.5). Alternatively, the acid solution may be diluted with water to raise the pH enough for separating the hydrate. Representative base includes organic base (e.g., triethylamine) and inorganic base (e.g., ammonium hydroxide, sodium hydroxide, potassium hydroxide, sodium carbonate, potassium carbonate, sodium hydrogen carbonate, potassium hydrogen carbonate), in which water soluble ones are conveniently handled, although it is not limited to these. A base insoluble in water (e.g., anion exchange resins) can also be used for this purpose.

(7) Crystallization

For separating or ripening the crystalls, the suspension of the separating crystals is preferably continued to be stirred for 10 minutes to 50 hours at 0° to 70° C. (especially at 5° to 35° C.).

(8) Drying

The drying is preferably done under a mild condition by drying (e.g., stationary, through flow, circulation, or fluidized bed drying) in an inert gas (e.g., air, nitrogen, carbon dioxide) at relative humidity of not lower than 15% at about room temperature (e.g., about 0° to 60° C.) under atmospheric pressure depending on the agitating or powder flow condition.

Under laboratory scale, the following have been observed: For example, in the case of drying in a closed container under atmospheric pressure, water content reaches to the first plateau corresponding to dihydrate in air of relative humidity of 15 to 50% (especially 20 to 30%) at 25° to 60° C. within 1 to 8 hours and the second plateau corresponding to trihydrate in air of relative humidity of 45% or more (especially 60 to 80%) at 25° to 60° C. (especially 10° to 25° C.) for 1 to 8 hours.

In the case of a through flow or circulation dryer, depending on the agitating or powder flow condition, for example, the through flow drying in air of relative humidity 50 to 60% at 25° to 40° C. until the inflection point of the time versus outlet air temperature curve or time versus outlet air humidity curve (about 2 to 10 hours when the starting material contained 30 to 60% of water) gives a product corresponding to dihydrate as the main component.

In the case of a fluidized bed dryer, depending on the air blow condition, for example, the drying in air of relative humidity 50% to 60% at 10° to 35° C. (especially 20° to 30° C.) until the first inflection point of the time versus outlet air temperature or time versus outlet air humidity curve (about 1 hour when the starting material contained 30 to 60% of water) gives a product corresponding to trihydrate and that until the second inflection point of the same (about 1.5 hour when the starting material contained 30 to 60% of water) gives a product corresponding to dihydrate as the main component.

For a large scale production, the circulation drying, through flow drying, and fluidized bed drying can suitably be applied.

In a representative case of fluidized bed dryer, depending on the flow rate of the air per wet crystal weight or other conditions, the drying in air at relative humidity 20 to 80% (especially 50 to 60%) at 10° to 60° C. (especially 20° to 30° C.) until the first inflection point of the time versus outlet air temperature or time versus outlet air humidity curve (about 1 to 5 hour when the starting material contains 30 to 60% of water) gives crystalline trihydrate and that until the second inflection point (about 3 to 7 hour when the starting material contains 30 to 60% of water) gives crystalline dihydrate as the main component.

Drying at higher than about 60° C. in the presence of a drying agent, under reduced pressure or the like severe conditions lowers the crystalline water less than two to afford unstable product (e.g., drying under 0.01 mmHg over calcium chloride at 25° to 28° C. lowers the water content down to 1.5 to 4.8% within 3 hour; drying in dry nitrogen circulation at 25° C. within 30 minutes lowers the water content down to 1.08%).

[Stability of the crystalline hydrate]

The stability of the crystalline hydrate of this invention was confirmed by an acceleration test showing 97.8% retention of potency after 1 month as compared with the value (73.6%) of anhydrous material.

[Use of the crystalline hydrate]

A pharmacologically effective amount of the crystalline hydrate of this invention can be used in a form of oral composition (especially capsules, granules, tablets) for preventing or treating bacterial infections. Alternatively, the crystalline hydrate can be stored for further processing after certain period of time.

[II]

SEALED CAPSULES

[The sealed capsules]

The inventors seeked for a composition capable of keeping the 7432-S hydrates stable for a long time without excessive cost and found that the hydrate filled in a gelatin hard capsule sealed with a gelatin band showed far less color change and potency loss.

[Method for producing the capsules]

The capsules of this invention can be prepared by mixing a pharmacologically effective amount of the hydrate with an additive (e.g., bulking agent, lubricant), then filling in a capsule, applying aqueous solution of gelatin around the circumference of entire joint of cap and body of the capsule, and drying to form a gelatin band.

The gelatin hard capsule may be a usual commercial capsule without specific limitation in size or color. It may contain dyestuff and/or pigment.

Although any additive (e.g., bulking agent or lubricant) is no requisite for protecting the hydrate from coloration or loss of potency, it is preferably used for better handling for filling a pharmacologically effective amount of the hydrate in a capsule. The bulking agent can be a usual one for powder or granules, e.g., sugar (e.g., glucose, fructose, lactose), starch (e.g., corn starch, potato starch), or cellulose (e.g., crystalline cellulose, methylcellulose, methylethylcellulose). The lubricant can be a usual one for powder, granule or tablet, e.g., purified talc, stearic acid or its salt (e.g., sodium, magnesium, or calcium salt), borax, liquid paraffin, sodium benzoate, polyethyleneglycol (average molecular weight: 6000), carnauba wax, or hydrogenated oil.

The aqueous solution of gelatin may be prepared by dissolving 10 to 30% (preferably 15 to 25%) of gelatin in water optionally containing 1 to 40% of lower alkanol (e.g., 20 to 30% of methanol, ethanol, propanol, or glycerin), ether (e.g., 0.5 to 10% of polyoxyethylene sorbitan monooleate=Polysorvate), ketone, or ester in a conventional manner to enable the solution be applied at the joint of capsule and dried (e.g., by air stream or heat) at 0° to 80° C. Usually, 5 to 50 mg of the gelatin solution optionally containing a pharmaceutically acceptable pigment is applied on a gelatin capsule of size No. 2 to 4.

[EXAMPLES]

The following examples and experiments illustrate this invention. They are, however, not to be construed to limit the scope of this invention. The content of water was determined by the Karl-Fischer method.

[I]

HYDRATES

EXAMPLE 1

A solution of crude 7432-S (25 g) in 6N-hydrochloric acid (75 ml) is let stand for 1 hour at 15° to 20° C. to separate hydrochloride. The crystals are collected by filtration, washed with acetonitrile (75 ml) containing 1 drop of concentrated hydrochloric acid, and dried to give crystalline 7432-S hydrochloride monohydrate (18 g).

A solution of this monohydrate (1.0 g) in 3N-hydrochloric acid (4 ml) is adjusted to pH 1.5 by adding water (30 ml) and a base and stirred for 2.5 hours at 25° to 45° C. The separating crystals are collected by filtration and washed with water. The crystals are dried with a circulation dryer at 10° C. for 5 hours to give crystalline 7432-S hydrate (0.7 g) of water content 10.2%. Ratio of geometric isomers (cis/trans)=98.8:0.2.

EXAMPLE 2

Crude crystalline 7432-S (1.17 g) is suspended in a mixture of t-butanol (3 ml) and acetonitrile (3 ml). To this suspension is added 35% hydrochloric acid (1 ml; 5 molar equivalents) to give a solution. This solution is diluted with a mixture of t-butanol (3 ml), acetonitrile (9 ml), and water (5 ml), adjusted to pH 2.3 with triethylamine, and stirred for 3 hours at 30° to 35° C. The separating crystals are collected, washed with a mixture of acetonitrile, t-butanol, and water (2:1:1; 5 ml) and water (10 ml) and dried with a through flow dryer at 25° to 30° C. for 2 hours to give crystalline hydrate (1.06 g) of water content 8.75%. Ratio of geometric isomers (cis/trans)=99.2:0.8.

EXAMPLE 3

To a suspension of crude crystalline 7432-S (1.0 g) in a mixture of water (8 ml) and acetonitrile (1 ml) is added sodium hydrogen carbonate (0.41 g; 2 molar equivalents) giving a clear solution. This solution is diluted with methanol (6 ml), treated with active charcoal (0.1 g), stirred at room temperature for 10 minutes, and filtered to remove the active charcoal. The filtrate is acidified with 6N-hydrochloric acid (1.62 ml; 4.5 molar equivalents) and poured into a mixture of water (3.4 ml) and acetonitrile (5 ml). The mixture is adjusted with 30% potassium carbonate to pH 2.3, stirred for 1 hour at 40° C. and for 1.5 hours at 20° to 25° C. The separating crystals are collected, washed with a mixture of methanol, acetonitrile, and water (1:1:2; 5 ml), water (20 ml), and methanol (5 ml) successively and dried by through flow drying at 20° to 25° C. for 1.5 hours to give crystalline hydrate (0.876 g) of water content 9.35%. Ratio of geometric isomers (cis/trans)=99.6:0.4.

EXAMPLE 4

To a solution of sodium hydrogen carbonate (1.848 g; 3 molar equivalent) in water (42 ml) is added crude crystalline 7432-S (4.66 g). The solution is treated with acetonitrile (19 ml), active alumina (2.34 g), and active charcoal (0.466 g), stirred at 15° to 20° C. for 30 minutes, and filtered to remove the active carbon and alumina. The filtrate is poured into a mixture of acetonitrile (37 ml), 62% sulfuric acid (3.95 g), and water (28 ml). The mixture is diluted with aqueous 30% potassium carbonate at 20° to 25° C. to adjust pH 3.0 and stirred for 30 minutes at the same temperature. The separating crystals are collected by filtration and dried by circulation drying at 20° to 25° C. for 2 to 3 hours to give crystalline hydrate (4.384 g) of water content 12.2%. Ratio of geometric isomers (cis/trans)=99.6:0.4.

Under similar condition, a solution of 7432-S (1.0 g) in aqueous sodium hydrogen carbonate (12 ml) is treated with active alumina and active carbon. The solution is diluted and acidified with a solvent (water, isopropanol, or acetonitrile; 6 ml) and 85% phosphoric acid (8 molar equivalents), successively, then adjusted to pH 3.0 with aqueous 30% potassium carbonate at 20° to 25° C., and stirred at the same temperature for 30 minutes. The separating crystals are collected by filtration, and dried by through flow drying at 20° to 25° C.

for 2 to 3 hours to give crystalline hydrate (about 0.90 g) of water content 11.0%. Ratio of geometric isomers (cis/trans)=99.2 to 99.7/0.8 to 0.3.

Under the same condition but substituting phosphoric acid with methanesulfonic acid (4 molar equivalents), crystalline hydrate (0.879 g) is produced. Water content: 11.4%. Ratio of geometric isomers (cis/trans)=99.6/0.4.

EXAMPLE 5

To a suspension of crude crystalline 7432-S (2.0 g) in a mixture of dimethoxyethane (18 ml) and ethanol (2 ml) is added 6N-hydrochloric acid (0.89 ml; 1.3 molar equivalents) at 2° to 5° C., and the mixture is stirred at the same temperature for 2 hours. The separating crystals of hydrochloride are collected by filtration, washed with a mixture (10 ml) of dimethoxyethane and ethanol (9:1) and acetonitrile (10 ml), and dried at 25° to 30° C. for 2 hours to give hydrochloride (1.878 g).

A suspension of this hydrochloride (1.0 g) in a mixture of methanol (6 ml) and water (5 ml) is dissolved by adding sodium hydrogen carbonate (0.61 g; 3 molar equivalent) giving a solution. To this solution is added active carbon (0.1 g), stirred at 25° to 30° C. for 10 minutes, and filtered to remove the active carbon. The filtrate is poured into a mixture of 35% hydrochloric acid (1.01 ml; 4 molar equivalents), water (3 ml), and acetonitrile (6 ml), adjusted its pH to 3.0 with aqueous 30% potassium carbonate, and stirred at 25° to 30° C. for 30 minutes and 5° to 7° C. for 1 hour. The separating crystals are collected by filtration, washed with ethanol (5 ml) and water (10 ml) successively, and dried by through flow drying at 20° to 25° C. for 2 hours to give crystalline hydrate (0.82 g) of water content 10.6%. Ratio of geometric isomers (cis/trans)=99.5:0.5.

EXAMPLE 6

To a solution of sodium hydrogen carbonate (1.3 g; 2.2 molar equivalents) in water (18 ml) is added crude crystalline 7432-S (3.0 g). The solution is treated with active alumina (1.5 g) and active charcoal (0.3 g), stirred at 20° to 25° C. for 30 minutes, and filtered to remove the active carbon and alumina. The filtrate is poured into a mixture of malic acid (10 molar equivalents), (17 ml) and acetonitrile (36 ml). The mixture is neutralized with aqueous 30% potassium carbonate at 20° to 25° C. to adjust pH at 3.0 and stirred for 30 minutes at the same temperature. The separating crystals are collected by filtration and dried by circulation drying at 20° to 30° C. for 2 hours to give crystalline hydrate (2.665 g) of water content 11.7%. Ratio of geometric isomers (cis/trans)=99.1:0.9.

Under the same condition but substituting malic acid with fumaric acid (10 molar equivalents), crystalline hydrate of water content 10.1% is produced.

Similarly, a solution of 7432-S (1.0 g) in aqueous sodium hydrogen carbonate is treated with active alumina and active carbon. The solution is mixed with a solution of formic acid (4 molar equivalents) in aqueous acetonitrile. The mixture is treated as above to give crystalline hydrate (0.925 g) of water content 12.7%. Ratio of geometric isomers (cis/trans)=99.8:0.2.

The said amount of formic acid can be increased up to 75 molar equivalents to give the same crystalline hydrate.

EXAMPLE 7

A sample of 7432-S hydrate (1 g) prepared by the method of Example 3 is placed respectively in a tightly closed container fixing its relative humidity at 0%, 12%, 20%, 44%, 57%, or 75% by selecting a suitably wet drying agent and kept at room temperature for 6 hours. Then the water content of each sample is determined by Karl-Fischer method to give the value of 1.05%, 5.83%, 8.54%, 11.21%, 12.19%, and 12.21%, respectively.

The values show that the main component is dihydrate (calcurated water content=8.07%) at relative humidity 20% and trihydrate (calcurated water content=11.64%) at relative humidity higher than 44%.

When this drying is continued further 30 hours, the loss of water content from 6 to 30 hours is less than 0.2% in the case of relative humidity higher than 20%.

EXAMPLE 8

A sample of 7432-S (1 g) prepared by the method of Example 3 is placed respectively in a tightly closed container fixing its relative humidity at 20%, 44%, 57%, or 75% by selecting a suitably wet drying agent kept at 40° C. for 1 month. Then the water content of each sample is determined by Karl-Fischer method to give the value of 7.92%, 10.69%, 11.73%, and 12.4%, respectively. The loss of water content from 30 hours to 1 month is less than 0.5% to show stable water content.

[II]

SEALED CAPSULES

In the following Examples 9 to 14 and reference examples 1 to 6, 7432-S hydrate is in a crystalline form containing about 10% of crystal water when assayed by Karl-Fischer method.

EXAMPLE 9

The hydrate (1 kg), crystalline cellulose (1.18 kg), and magnesium stearate (0.02 kg) (each as 60 mesh powder) are mixed for 20 minutes using a 10 liter V-type mixer. The mixed powder (253 mg each) is filled in a white gelatin hard capsule No. 2 containing titanium dioxide (3.5%). Then, the sealing gelatin solution [17 to 26 mg at 60° C.; an aqueous solution of gelatin (21.13%) and Polysorvate 80 (2%)] is applied along the circumference at the joint of cap and body of capsule (using a Hard capsule sealing machine S-100 distributed by Japan Elanco Company) and dried for 5 minutes at room temperature under air stream. The product contains 100 mg potency of 7432-S per capsule.

EXAMPLE 10

The hydrate (1 kg), lactose (1.9 kg), and hydrogenated caster oil (0.1 kg) (each as 60 mesh powder) are mixed for 20 minutesusing a 10 liter V.-type mixer. The mixed powder (172 mg each) is filled in a white gelatin hard capsule No. 2 containing titanium dioxide (6%). Then, the sealing gelatin solution [20 to 25 mg at 55° C.; an aqueous solution of gelatin (22%), glycerin (5%), and ethanol (30%)] is applied along the circumference at the joint of cap and body of capsule (using a Hard capsule sealing machine S-100 distributed by Japan Elanco Company) and dried for 5 minutes at room temperature under air stream. The product contains 50 mg potency of 7432-S per capsule.

EXAMPLE 11

The hydrate (1 kg), crystalline cellulose (0.5 kg), and pulverized carnauba wax (0.02 kg) (each as 60 mesh powder) are mixed for 20 minutes using a 10 liter V-type mixer. The mixed powder (171 mg each) is filled in a white gelatin hard capsule No. 4 containing titanium dioxide (2.1%). Then, the sealing gelatin solution [10 to 20 mg at 60° C.; an aqueous solution of gelatin (22%) and Polysorvate 80 (2%)] is applied around the circumference at the joint of cap and body of capsule (using a Hard capsule sealing machine S-100 distributed by Japan Elanco Company) and dried for 4 minutes at room temperature under air stream. The product contains 100 mg potency of 7432-S per capsule.

EXAMPLE 12

A capsule is produced by the method of Example 9 except for using transparent gelatin hard capsule No. 4.

EXAMPLE 13

A capsule is produced by the method of Example 9 except for using non-transparent blue gelatin hard capsule No. 4 containing trace blue dye No. 1, red dye No. 3, and titanium dioxide.

EXAMPLE 14

A capsule is produced by the method of Example 9 except for using non-transparent red gelatin hard capsule No. 4 containing trace blue dye No. 1, red dye No. 3, yellow dye No. 5 and titanium dioxide.

REFERENCE EXAMPLE 1

The hydrate (1 kg), crystalline cellulose (1.08 kg), benzyl hydroxy anisole as antioxidant (10 mg of 60 mesh powder) and magnesium stearate (0.02 kg) were mixed for 20 minutes in 10 liter V-type mixer. The mixed powder (253 mg each) was filled in a white gelatin hard capsule No. 2 containing 3.5% titanium dioxide. The product contained 100 mg potency of 7432-S per capsule.

REFERENCE EXAMPLE 2

The hydrate (1 kg), crystalline cellulose (1.18 kg), and magnesium stearate (0.02 kg) (each as 60 mesh powder) were mixed for 20 minutes in 10 liter V-type mixer. The mixed powder (253 mg each) was filled in a white gelatin hard capsule No. 2 containing titanium dioxide (3.5%). The product contained 100 mg potency of 7432-S per capsule.

REFERENCE EXAMPLE 3 TO 6

A capsule each of Examples 11 to 14 prior to applying the sealing gelatin solution was designated as the capsules of Reference examples 3 to 6 for the following experiments.

EXPERIMENTS FOR CAPSULES

The following experiments show stability of the composition observed under HPLC condition: Column=Polygosil $60_{10}C_{18}$ 4 mm$\phi \times$250 mm (M. Nagel & Co.); Mobile phase=aqueous 0.05M ammonium acetate/methanol (96/4); Flow rate=1.5 ml/minute; Internal standard=nicotinamide; and UV determination=at 254 nm.

EXPERIMENT 1

The capsule (10 capsules each) was placed in 500 ml glass container, stoppered tightly, and kept in a chamber at 45±1° C. The content of 7432-S was determined monthly for 4 months by HPLC.

The content in Table 2 shows retention in percent as compared with the content of freshly produced capsules.

A capsule without the sealing, regardless of presence of an antioxidant as a stabilizing agent, was apparently more unstable as compared with that of this invention.

TABLE 2

| Capsule | | Content (%) Month | | | |
|---|---|---|---|---|---|
| | | 1 | 2 | 3 | 4 |
| This invention | Example 9 | 99.4 | 96.5 | 94.2 | 91.8 |
| | Example 10 | 98.0 | 95.8 | 93.4 | 91.2 |
| Reference | Reference example 1 | 96.7 | 93.0 | 86.3 | 81.4 |
| | Reference example 2 | 94.5 | 89.4 | 87.3 | 80.4 |

EXPERIMENT 2

The capsule (10 capsules each) put on white and thick paper was kept in a chamber at 25±1° C. and irradiated under a fluorescent lamp of 10,000 Lux. The content of 7432-S was determined monthly for 2 months by HPLC and the color change in NBS color difference unit by using a color difference meter (Color-studio of Nihon Densyoku Kogyo).

Table 3 shows the retention of the content and color change in NBS unit as compared with those of freshly produced capsules.

TABLE 3

| Capsule | | Content (%)/NBS unit Month | |
|---|---|---|---|
| | | 1 | 2 |
| This invention | Example 11 | 99.7/0.68 | 100.2/1.47 |
| | Example 12 | 100.1/1.35 | 100.0/2.85 |
| | Example 13 | 100.1/0.07 | 99.8/3.00 |
| | Example 14 | 99.7/0.04 | 100.1/2.61 |
| Reference | Reference example 3 | 98.3/1.62 | 98.0/6.98 |
| | Reference example 4 | 97.0/4.06 | 96.1/7.39 |
| | Reference example 5 | 98.8/3.23 | 98.3/8.12 |
| | Reference example 6 | 99.6/0.87 | 99.8/4.65 |

NBS unit is a unit of color difference according to the U.S. National Bureau of Standards. The following list shows general idea of the values versus appearance.

From these experiments it is concluded that the compositions of this invention keeps 7432-S stable even under accerelating condition (e.g., heat, irradiation) and protects it from color change. Contrasting colors for capsule and sealing solution, as they may freely be selected, enable easy detection of a broken band sealing.

LIST

| NBS unit | difference | NBS unit | difference |
|---|---|---|---|
| 0~0.5 | insignificant | 3.0~6.0 | remarkable |
| 0.5~1.5 | slight | 6.0~12.0 | apparent |
| 1.5~3.0 | significant | >12.0 | very |

What we claim is:
1. A process for the preparation of a crystalline hydrate of 7-β-[(Z)-2-(2-aminothiazol-4-yl)-4-carboxybut-

2-enoylamino]-3-cephem-4-carboxylic acid having the X-ray diffraction pattern as follows:

| d | I/I$_o$ | d | I/I$_o$ | d | I/I$_o$ | d | I/I$_o$ |
|---|---|---|---|---|---|---|---|
| 5.90 | 12 | 20.95 | 100 | 28.70 | 17 | 35.93 | 08 |
| 7.35 | 08 | 21.15 | 70 | 29.40 | 27 | 36.38 | 24 |
| 9.45 | 92 | 21.75 | 25 | 29.60 | 11 | 37.00 | 07 |
| 10.15 | 21 | 22.25 | 49 | 29.90 | 16 | 38.30 | 26 |
| 12.08 | 46 | 23.85 | 62 | 30.40 | 19 | 38.65 | 10 |
| 14.87 | 30 | 24.50 | 39 | 31.10 | 53 | 39.20 | 15 |
| 15.65 | 14 | 24.80 | 16 | 31.60 | 23 | 39.60 | 21 |
| 16.25 | 13 | 25.50 | 34 | 31.78 | 34 | 40.27 | 15 |
| 18.35 | 24 | 25.85 | 66 | 33.02 | 28 | 41.22 | 22 |
| 18.90 | 71 | 26.60 | 16 | 33.55 | 23 | 42.55 | 08 |
| 19.14 | 77 | 27.02 | 59 | 33.86 | 17 | 44.20 | 09 |
| 19.40 | 60 | 27.30 | 35 | 35.20 | 16 | | |
| 20.58 | 88 | 28.35 | 54 | 35.65 | 10 | | | which comprises dissolving 7β-[(Z)-2-(2-aminothiazol-4-yl)-4-carboxybut-2-enoylamino]-3-cephem-4-carboxylic acid in aqueous acid, raising the pH of the solution to about 1.5 to 5 at about room temperature to form crystals, separating the wet crystals and drying the crystals until the first inflection point of the time versus outlet air temperature curve or the time versus outlet air humidity curve is reached to give the trihydrate or until the second inflection point of the same to give the dihydrate.

2. A process as claimed in claim 1 wherein the drying is carried out by stationary, through flow, circulation, or fluidized bed drying in an inert gas at relative humidity of not lower than 15% at 0° to 60° C.

3. A process as claimed in claim 1 wherein the drying is carried out with a through flow dryer using air of relative humidity 50 to 60% at 25° to 40° C.

4. A process as claimed in claim 1 wherein the drying is carried out with a fluidized bed dryer using air of relative humidity 50% to 60% at 10° to 35° C.

5. A process as claimed in claim 1 wherein the wet crystals are prepared by raising pH of an aqueous acid solution of the compound for crystallization and by ripening of crystals.

6. A process as claimed in claim 5 wherein concentration of the starting material in the aqueous acid solution is between 2.0 and 15.0%.

7. A process as claimed in claim 5 wherein the raising pH of the aqueous acid solution is effected with triethylamine, ammonium hydroxide, sodium hydroxide, potassium hydroxide, sodium carbonate, potassium carbonate, sodium hydrogen carbonate, potassium hydrogen carbonate, or anion exchange resins or by dilution with water.

8. A process as claimed in claim 5 wherein the ripening of crystals is continued for 10 minutes to 50 hours at 0° to 70° C.

* * * * *